(12) United States Patent
Larsen et al.

(10) Patent No.: US 8,257,778 B2
(45) Date of Patent: Sep. 4, 2012

(54) METHOD OF MANUFACTURING FIBROUS HEMOSTATIC BANDAGES

(75) Inventors: Gustavo Larsen, Lincoln, NE (US); Ruben Spretz, Lincoln, NE (US); Raffet Velarde-Ortiz, Lincoln, NE (US)

(73) Assignee: LNK Chemsolutions, LLC, Lincoln, NE (US)

( * ) Notice: Subject to any disclaimer, the term of this patent is extended or adjusted under 35 U.S.C. 154(b) by 0 days.

(21) Appl. No.: 13/414,949

(22) Filed: Mar. 8, 2012

(65) Prior Publication Data

US 2012/0171355 A1     Jul. 5, 2012

Related U.S. Application Data

(63) Continuation of application No. 12/281,588, filed as application No. PCT/IB2007/050107 on Jan. 13, 2007, now abandoned.

(60) Provisional application No. 60/743,866, filed on Mar. 28, 2006.

(51) Int. Cl.
*A61F 13/02*     (2006.01)

(52) U.S. Cl. ........... 427/2.31; 95/280; 424/426; 602/56; 264/449; 427/2.1; 427/180

(58) Field of Classification Search .................. 264/449; 95/280; 424/426; 602/256; 427/2.31, 180
See application file for complete search history.

(56) References Cited

U.S. PATENT DOCUMENTS

| | | | |
|---|---|---|---|
| 6,596,296 B1 * | 7/2003 | Nelson et al. | 424/426 |
| 2002/0059868 A1 * | 5/2002 | Gogins et al. | 95/280 |
| 2005/0240137 A1 * | 10/2005 | Zhu et al. | 602/56 |

* cited by examiner

*Primary Examiner* — Dah-Wei Yuan
*Assistant Examiner* — Andrew Bowman
(74) *Attorney, Agent, or Firm* — Louis Ventre, Jr.

(57) ABSTRACT

A method of manufacturing a sturdy and pliable fibrous hemostatic dressing by making fibers that maximally expose surface area per unit weight of active ingredients as a means for aiding in the clot forming process and as a means of minimizing waste of active ingredients. The method uses a rotating object to spin off a liquid biocompatible fiber precursor, which is added at its center. Fibers formed then deposit on a collector located at a distance from the rotating object creating a fiber layer on the collector. An electrical potential difference is maintained between the rotating disk and the collector. Then, a liquid procoagulation species is introduced at the center of the rotating disk such that it spins off the rotating disk and coats the fibers.

14 Claims, 2 Drawing Sheets

METHOD OF MANUFACTURING FIBROUS HEMOSTATIC BANDAGES

CROSS-REFERENCE TO RELATED APPLICATIONS

The present invention is a continuation of U.S. patent application Ser. No. 12/281,588 filed 3 Sep. 2008, which is a 371 national stage of PCT/IB2007/50107, filed 13 Jan. 2007, which claims the benefit of U.S. provisional application 60/743,866 filed 28 Mar. 2006, the text of which are hereby incorporated by reference herein.

GOVERNMENT LICENSE RIGHTS

The U.S. Government has a paid-up license in this invention and the right in limited circumstances to require the patent owner to license others on reasonable terms as provided for by the terms of contract No. 2004-02653 awarded by the United States Department of Agriculture, contract No DOE DE-FG02-05ER84326 awarded by the U.S. Department of Energy and contract No. W81XWH-05-1-0527 awarded by the U.S. Army, all with LNK Chemsolutions, LLC as a Subcontractor.

TECHNICAL FIELD

This invention relates to a method of manufacturing hemostatic compositions useful in reduction and cessation of blood loss from battlefield injuries, surgical procedures and traumatic wounds.

BACKGROUND ART

This invention complements another invention titled, "Methods for Making a Multicomponent Hemostatic Dressing," disclosed in patent application PCT/IB2006/053526 filed on 27 Sep. 2006, which is incorporated by reference herein. That invention discloses a method of making a fibrous, pliable, bioabsorbable hemostatic dressing in which one of the process steps involves forming fibers from the homogeneous mixture, which essentially is the step that creates the fibrous base of the bandage, also referred to as the backing or scaffolding of the dressing. The present invention sets forth a new method of forming the fibers compatible with this earlier invention. In addition, the present invention can be used independently to manufacture a multi-component hemostatic bandage. As importantly, the present invention enables manufacture of a bandage with a high surface area per unit weight of exposed active ingredients to rapidly effect blood clotting in a wound.

Hemostatic compositions of the present invention are also generally referred to as bandages or wound dressings. During the three decades preceding this invention, an understanding of the human immunodeficiency virus (HIV) and hepatitis propagation risks stemming from use of unpurified blood and blood derivatives hindered the safe development of human fibrinogen-based hemostatic bandages. However, later improvements on recombinant fibrinogen and recombinant blood factors technologies, as well as on plasma purification techniques, reopened opportunities for hemostatic bandage development.

Fibers for bandages are typically made by methods, such as melt blowing, extrusion, other fiber drawing techniques, and electrostatic spinning, or simply electrospinning. In this last method, a polymer is dissolved in a solvent or melted and placed in a glass pipette tube as a precursor liquid, that is, a fiber-forming liquid composition used to make the fibers. A tapered orifice or nozzle at one end of the tube is used to spin out or spray out a liquid stream that forms a fiber. A high voltage potential up to 50 kilovolts is applied between the polymer solution and a collector near the nozzle. This process can produce nanofibers with diameters as low as 50 nanometers, although the collected web usually contains fibers with varying diameters from 30 nanometers to over one micron. The production rate of this process is slow and often measured in quantities that are less than one gram per hour per nozzle, and the fiber strength is usually low, creating a fragile fiber.

Methods of electrospinning fibers for dressings that contain coagulation proteins are also well known. For example, United States Patent Application Publication No. 20060013863 A1 to S. W. Shalaby, et al., describes such methods and the formation of hemostatic, compliant, elastomeric, multicomponent, fibrous dressings. This prior art, however, does not teach a micrometer or sub-micrometer scale coating of the fibers. Rather, Shalaby teaches achieving bicomponent fibers through controlling the polymer molecular weight; the type of spinning solvent and hence, the solvent-polymer interaction; the concentration of the individual polymers; and the electrospinning parameters. These fiber fabrication techniques are different from the present invention and the core and sheath fiber produced do not have dispersion of the active at or near molecular level, so that there are no core-sheath distinctive regions in the fibers produced according to the present invention.

Despite this prior art, electrospinning of aqueous protein solutions is generally problematic because the chemical solution compromises the chemical stability or shelf-life of the proteins. One approach to overcome this shortcoming is spinning the bandage right on the wound at the time it is needed. PCT application WO/1998/003267 by R. A. Coffee, is an example. Electrospinning a bandage directly on a wound had an initial appeal of making the fibers directly off blood coagulation proteins, avoiding a fibrous backing and minimizing protein stability or shelf-life problems in pre-made bandages. However, practical problems in using this approach in situations involving arterial bleeding are that it is time consuming and requires a level of skill not often present in environments such as the battlefield. For direct application by electrospinning of aqueous protein solutions to wounds, two additional problems became evident: this electrospinning approach uses a lot more protein than by just coating biocompatible polymer fibers, such as those made from polylactic acid; and, electrospinning of proteins in fluorinated hydrocarbons is cell-toxic if even a trace fluorinated hydrocarbon remains in the fibers. The present invention does not make a dressing or bandage at the time it is needed at the emergency situation. Rather it is suited only for making the dressing in a manufacturing facility, packaging it, and shipping it for later use.

The method of the present invention uses a rotating disk and does not use a nozzle to create fibers of a bandage. These fibers may form the entire bandage or may be used as the scaffolding or fibrous backing in other bandage processing steps. Dressings produced according to the invention are characterized by the proximity of the different procoagulation constituents that would otherwise react prematurely on molecular contact. The fibers created by the method are pliable and much stronger than otherwise achievable for effective dressings. Another important characteristic of the present invention is a substantially higher manufacturing rate for fibers than conventional flow-through-orifice electrospinning and electrospray methods.

The present invention offers the capability of incorporating, on molecular-, micrometer- and sub-micrometer-scales, pro-coagulation species, either natural or synthetic, into the fiber-forming liquid composition used to make the fibers, and this is a desirable improvement. In addition, fibrinogen and/or other blood clotting species are incorporated in a micrometer or sub-micrometer scale coating on the fibers of the dressing. Fiber coatings of this scale typically means a coating thickness from about five to one hundredth of a micrometer.

In the present invention, fiber forming liquid is introduced at or near the center of a rotating disk such that fibers are spun off the rim of the disk. Use of a rotary device ensures adequate bandage production rates. Perhaps as importantly, the rotary device equipped with multiple feed lines, permits rapid customization of the fibers in a backing using one apparatus, simply by turning off one feed line and turning on another. This is important in that it allows for rapidly changing the fiber composition for a single bandage, for example in a sequential fashion, to include pro-coagulation species in a first set of fibers that would otherwise chemically react or conflict with the pro-coagulation species in a second set of fibers if used together.

A significant component of prior art that includes fibrinogen or other blood clotting species in a dressing are not fiber coatings, but are typically in multiple layers on the overall bandage, which is, generally, evident to the naked eye. A micrometer or sub-micrometer scale coating on the fibers is a more thorough distribution of the blood clotting species and cannot be discerned with the naked eye. In the prior art, the surface of each such distinct bandage layer exposes the blood clotting species to blood and surrounding air. Each such distinct layer has a characteristic dimension, such as thickness and grain size, that is larger than the average fiber diameter and the thickness of the coating of blood clotting species on any fibers in the present invention.

In a departure from the distinct bandage layer technology, U.S. Pat. No. 6,056,970 to K. E. Greenawalt, et al. teaches a fibrous dressing wherein the coagulation protein is dispersed throughout the hemostatic composition, but not in a molecular-scale coating on the bulk of the fibers in the dressing. Rather Greenawalt discloses dispersal within the fibers in a manner that captures comparatively larger domains of the protein within the fiber structure. Greenawalt also teaches compressing the fibers into paper-like compositions so as to prevent activation of fibrinogen during processing. The present invention is an improvement in that the protein is captured both within a fiber and as a micrometer or sub-micrometer scale coating on the fibers, such that it significantly increases the surface area of exposure of coagulation protein to the blood.

The method of the present invention offers significant manufacturing efficiencies in using a single apparatus to make a fibrous bandage with coated fibers. Avoiding processing steps that employ different equipment, provides efficiency and speed not available in the current state of the art.

The method of the present invention offers manufacturing flexibility in that different coating steps for the blood clotting species may be easily accomplished with the same apparatus. Essentially, what is required are separate feed lines for introducing the differing blood clotting species at the center of the rotating disk. In addition to flexibility, separate feed lines and separate coatings enable placement of the blood coagulation proteins in very close proximity to each other, even when such proteins cannot coexist together in solution or in intimate molecular contact. For example, fibrinogen and thrombin can be used in separate coatings without significant reaction into fibrin.

These capabilities translate to a substantially higher throughput than conventional flow-through-orifice electrospinning and electrospray methods. Both fiber backing and blood clotting species may be made and sequentially applied to a single bandage using the same apparatus, and flexibility in tailoring bandages for particular applications is enhanced by enabling choices in the order by which fiber and blood clotting species coating steps are introduced on the bandage.

As an example of such sequential application in a single bandage, the present invention enables formation of biopolymer fibers containing fibrinogen, and once dry, formation of biopolymer fibers containing of thrombin. This bandage, thus, has two dry layers of fiber containing different procoagulant species. The bandage is created using a single and modular bandage manufacturing unit operating continuously. The fibers made in each run can be made as thin as several micrometers each. Another example is biopolymer fibers made first then coated with fibrinogen, coated again with biopolymer to serve as a separation coating, then coated with thrombin.

Three key elements represent improvement over prior art dealing with fibrous thrombin-fibrinogen bandage structures. First, dispersion of the protein coatings in the micrometer and sub-micrometer range guarantee a high surface area per unit weight exposed to gushing blood coming off an arterial wound, which is essential for clot formation in the order of seconds. Second, proteins such as thrombin and fibrinogen that would otherwise initiate blood coagulation cascade reactions on molecular contact, thereby significantly reducing the shelf-life of the hemostatic bandage, are kept in separate coatings but, more importantly, at distances ranging from one micron to one millimeter to ensure very rapid interaction between these two coagulation cascade proteins on contact with blood from a wound. Third, the ultrafine biocompatible fiber backing is meant to provide a strong scaffolding effect during formation of a blood clot at the arterial wound site.

There are a number of synthetic agents that can potentially improve the performance of fibrinogen-based hemostatic bandages, besides natural ones such as thrombin, prethrombin, Factor XIIIa and other blood coagulation factors. Very recently, the use of propyl gallate and other gallate derivatives has been disclosed to increase the performance of fibrinogen-based hemostatic dressings with hemostatic dressing backings made, among other things, of collagen. U.S. Pat. No. 6,891,077 to S. W. Rothwell, et al., is an example disclosing this use. Propyl gallate is also used in the food industry as an antioxidant additive for oils and fats. The present invention newly creates the option of occluding propyl gallate and its derivatives within the fibers of the dressing. The Rothwell patent teaches a method of adding a solution of propyl gallate to a bandage, but does not teach using propyl gallate dispersed into the bulk of fibers.

The United States Army has recently used a fibrinogen bandage with a chitosan backing in the battlefield. Besides chitosan, which is a biopolymer derived from the chitin in crustaceans, other polymers such as but not limited to polylactic acid and polylactic-co-glycolic acid and combinations thereof, may be viewed as good fiber precursors for a fibrinogen-containing wound dressing. Polylactic acid and polylactic-co-glycolic acid degrade in vivo by hydrolysis (esterase activity) into lactic acid and glycolic acid, respectively, which are then incorporated into the tricarboxylic acid metabolic cycle. Besides polylactic acid and polylactic-co-glycolic acid, other bioabsorbable polymers such as, but not limited to, polycaprolactone, and copolymers resulting from combinations thereof, may be used as fiber precursors for hemostatic dressings and the present invention permits full utilization of these materials thoroughly mixed in the fibers of the bandage.

Fibrinogen has been recently processed into fibers by electrospinning from 1,1,1,3,3,3-hexafluoroisopropanol solutions. Besides being soluble in water, proteins are often soluble in perfluorinated alcohols such as 1,1,1,3,3,3-hexafluoroisopropanol, and 2,2,2-trifluoropropanol. The acute toxicity of 1,1,1,3,3,3-hexafluoroisopropanol, however, is well documented. Despite the acute toxicity problems, a number of patent applications still describe methods for direct electrospinning of protein solutions in organic solvents for making hemostatic and wound dressings. For example, two of these include United States Patent Application Publication Nos. 20040037813 for electrospun collagen and 20040229333 for electroprocessed fibrin.

The pouring of a fluid at or near the center of a rotating disk in the presence of electric fields as a means for liquid atomization is well known. Besides their traditional use for spraying paint, Balachandran and Bailey for example (W. Balachandran and A. G. Bailey, 'The Dispersion of Liquids Using Centrifugal and Electrostatic Forces', IEEE Transactions on Industry Applications, Vol. 1A-20, No. 3, 682-686 (1984)) described the modes by which hydrocarbon oils of varying resistivity values are accelerated from the edge of the rotating disk toward an annular counterelectrode.

This prior art does not teach the manufacture of a bandage nor does it describe the elements needed to create a functional hemostatic bandage composed of coated fibers or multicomponent fibers assembled into a dressing. The present invention applies a rotating disk apparatus under a innovative set of control conditions to manufacture a fibrous hemostatic bandage with attributes missing from, and needed to improve, the art of manufacturing hemostatic dressing.

DISCLOSURE OF INVENTION

Technical Problem

There is a need for a dressing that exposes blood to a large surface area per unit weight of coagulation protein, given that using large amounts of proteins from the coagulation cascade in a hemostatic dressing is cost-prohibitive for developing an efficient product for use in both military and civilian markets.

There is a need for a method of manufacturing fibers used for a hemostatic dressing that is fast and efficient in promoting blood clotting.

There is a need for a method of manufacturing fibers used for a hemostatic dressing that permits rapid customization of the fibers using one apparatus.

There is a need for a method of manufacturing of bandages that is reliable and capable of continuous production of fibers used for hemostatic dressings.

There is a need for a method of manufacturing fibers used for a hemostatic dressing that enables inclusion of blood clotting species within the fibers.

There is a need for a method of manufacturing fibers used for a hemostatic dressing that enables coating the fibers with blood clotting species.

There is a need for a method of manufacturing fibers used for a hemostatic dressing that are sturdy and pliable enough to adapt to the varieties of wound sites.

Technical Solution

A method of manufacturing a sturdy and pliable fibrous hemostatic dressing by making fibers that maximally expose surface area per unit weight of active ingredients as a means for aiding in the clot forming process and as a means of minimizing waste of active ingredients. The fibers of the dressing are coated with, or contain on a molecular scale within the fibers, active biological or abiological procoagulation species. The method employs a rotating disk surrounded by a collector between which there is an electrical potential difference. A liquid biocompatible fiber precursor is delivered at or near the center of the disk, which is rotating, preferably at a speed in a range of about 300 to 100,000 revolutions per minute. The liquid fiber precursor optionally contains one or more active biological or abiological procoagulation species. The preferred collector is made of wire mesh and the size of the mesh is determined according to the desired texture of the fibrous mat. The liquid fiber precursor that is delivered at or near the center of the disk is accelerated toward the edge of the disk by the combined action of both the electric field and centrifugal forces acting upon the rotating disk. A preferred electrical potential difference is in the range of 3 to 60 kilovolts, and the preferred flow range is about 5 to 5,000 milliliters per hour for disks with diameters in the range of 5 to 70 millimeters, and edge-of-disk to collector separations between 5 to 100 centimeters. The fibers are then optionally coated with a blood coagulation species. The coating step is performed by one of several techniques including (a) introducing the procoagulation species at the center of the rotating object such that said liquid can spin off the rotating object and coat the fibers; (b) spraying the fibers using dry or wet electrospraying; (c) soaking the fibers in a solution containing the procoagulation species causing wet impregnation of the fibers.

Advantageous Effects

The present invention solves the above noted technical problems. It enables manufacture of a bandage with a high surface area per unit weight of exposed active ingredients to rapidly effect blood clotting in the worst of wounds, such as wound characterized by arterial bleeding. Dressings produced according to the invention are characterized by the proximity of the different procoagulation constituents that would otherwise react prematurely on molecular contact.

The present invention enables the manufacture of fibers used for a hemostatic dressing at a faster rate than is possible using current nozzle- or orifice-based electrospinning methods and its scaffolding effects of the ultrafine fiber mats are especially important in blood clot formation in short times.

The present invention permits rapid customization of the fibers for a hemostatic dressing, optionally using one apparatus, while preventing procoagulation species in a first set of fibers from adversely reacting with the pro-coagulation species in a second set of fibers in the same backing.

The present invention provides a capability to manufacture separate bandages in a continuous manufacturing operation employing modular bandage manufacturing devices. Modularity assures that the invention can be deployed in a manufacturing setting in multiple, independently operating lines to create redundancy in bandage manufacturing and thus improve the efficiency and continued operation of the process even when one or more of the devices experiences operational problems.

The present invention enables blood clotting species to be included within the fibers used for a hemostatic dressing. It enables use of propyl gallate, its derivatives, and other abiological clot-aiding chemicals by dispersing these chemicals within the fibers used for a hemostatic dressing.

The present invention enables manufacture of biocompatible polymer fibers used for a hemostatic dressing that are sturdy and pliable enough to adapt to the varieties of wound sites. Folding a sub-millimeter thick fibrous hemostatic dressing prepared using the methods of the present invention would make a thicker, sturdier patch to treat a bleeding wound.

BEST MODE

Figure 1:
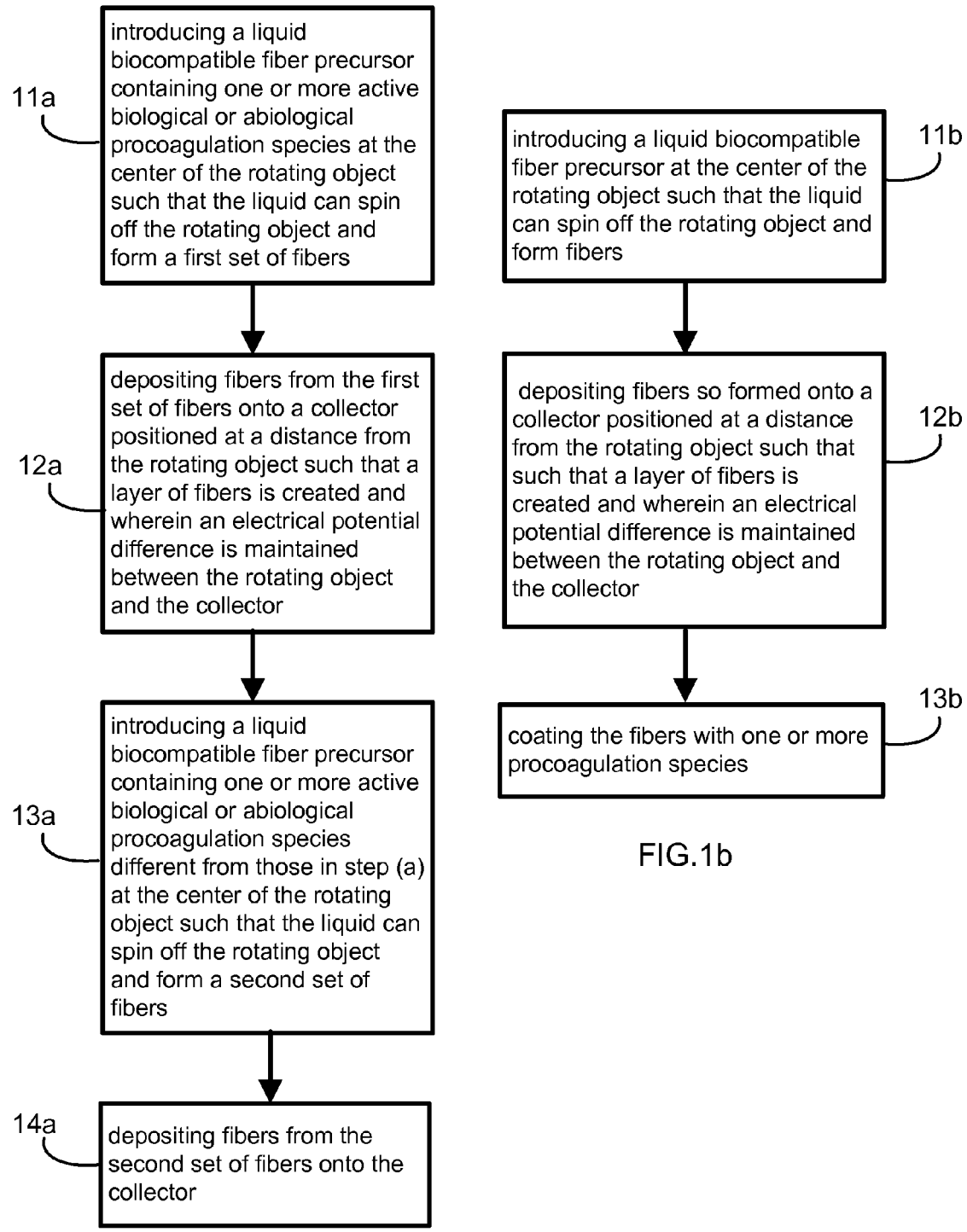
FIG. 1 is a block diagram of the steps of the preferred embodiments of the invention.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

Embodiments of the invention described herein use a liquid biocompatible fiber precursor, which is also referred to as biocompatible polymers in solution, to produce fibers that make up a hemostatic dressing. The term "liquid" is intended to have a broad definition. A liquid is typically obtained by suspending or dissolving one or more biocompatible fiber precursors in a solvent. The solvent may include therapeutics and processing aids. Thus, the term "liquid" encompasses a solution or suspension of biocompatible fiber precursor and may also contain therapeutic species, or combinations thereof.

Typical solvent solutions include ethyl acetate, glycerol, ethanol, water, acetone, plasticizers, polyethylene glycol, glycerol, other polyols, albumin, supercritical fluids, or their blends. An example of a supercritical fluid is carbon dioxide and water. Such solvents and processing aids are known in the art. The newest such solvents are super-critical fluids, which have been proposed as solvents for biocompatible fibers via electrospinning, as shown by Tepper, et al. at Virginia Tech "Supercritical CO2-Assisted Electrospinning," The Journal of Supercritical Fluids, 31(3), 329-334 (2005). Supercritical fluids are typically produced at very high pressures and high temperatures and behave like liquids for purposes of the present invention. A technological advantage in using supercritical fluids as a solvent, is that after the fibers have been made, the processing chamber is depressurized and the solvent is removed from the fibers by natural evaporation at the lower pressures.

The liquid biocompatible fiber precursor may contain biological or abiological blood clotting species, also referred to as procoagulation species or procoagulation ingredients. The fibers produced in accordance with the invention may also have a molecular-scale coating of a procoagulation species. When a dressing, which is made from the fibers made in accordance with the invention, makes first contact with blood, the blood is exposed to a significantly greater area per unit weight of blood procoagulation species than is possible with current dressings. Using any of the processes of the invention results in a pliable, biocompatible hemostatic dressing of fibers that promotes blood clotting when applied to a wound.

Preferred biocompatible fiber precursors are polylactic acid, polylactic glycolic acid, chitosan, chitin, polycaprolactone, poly ethylene oxide, poly ethylene glycol, modified and unmodified polysaccharides, modified and unmodified synthetic polyaminoacids, proteins, poly beta-hydroxybutyric acid), poly beta-hydroxyvaleric acid, polydioxanone, polyphosphazene, poly ethylene terephthalate, poly tartronic acid, poly malic acid, hemostatic proteins and combinations thereof. Random and block co-polymers resulting from the polymers listed in the preceding sentence may also be used. Other therapeutic agents that do not adversely affect the hemostatic function of the dressing may also be included.

Biological blood clotting species are natural proteins extracted from human or animal blood plasma that induce blood coagulation. Such proteins are also obtained from transgenic higher animals or via recombinant, genetic engineering methods using microorganisms. A preferred protein of such blood clotting species is fibrinogen. Human plasma fibrinogen almost invariably is molecularly associated with another blood clotting cascade, namely factor XIII, so a fiber coating of human-derived fibrinogen in a bandage according to the invention is accompanied by other blood clotting species, for example in a separate fiber coating or mixed within the fiber molecular structure. Other proteins of blood clotting species that may be used singly, or in combination only if the combination will not compromise the biological functionality of any protein constituent in the mixture when applied to a wound, are: thrombin, prothrombin, prethrombin, von Willebrand factor, factor XIII, factor XIIIa, fibronectin, fibrin, aprotinin, antiplasmin, alpha-2 macroglobulin, plasminogen, alpha-1-antitrypsin, and plasmin activator inhibitors, such as but not limited to, PAI-1 or PAI-2 and combinations thereof. Thrombin catalyzes the conversion of fibrinogen into fibrin in the presence of moisture, which is essentially the blood clot scaffold. So these two proteins may not be used together in the homogenous mixture either in the precursor or in a coating mixture, unless their aqueous solutions are handled at temperatures below zero degrees Celsius, as discussed in patent application PCT/IB2006/053526. Other proteins that adversely react when mixed together may not be combined in a mixture.

Abiological blood clotting species are non-protein chemicals that aid in blood clotting and clot stabilization and typically include calcium salts, propyl gallate and other gallic acid derivatives, epsilon aminocaproic acid, tranexamic acid, p-aminomethyl benzoic acid and other hemostatic medicaments. Propyl gallate and its chemical derivatives are considered to be blood platelet aggregation agents.

When a dressing of the present invention is applied to a wound, the procoagulation ingredients in or coating the fiber complement and supplement the coagulation-inducing proteins naturally present in blood released from a wound. These procoagulation ingredients interact chemically in the aqueous environment of the blood to rapidly promote formation of a clot. Blood plasma components called coagulation factors respond in a complex cascade to form fibrin strands. In an arterial wound, the rate-limiting factors for forming a strong clot within seconds to a few minutes is availability of procoagulation ingredients, especially fibrinogen and thrombin, in sufficient amounts.

Figure 2:
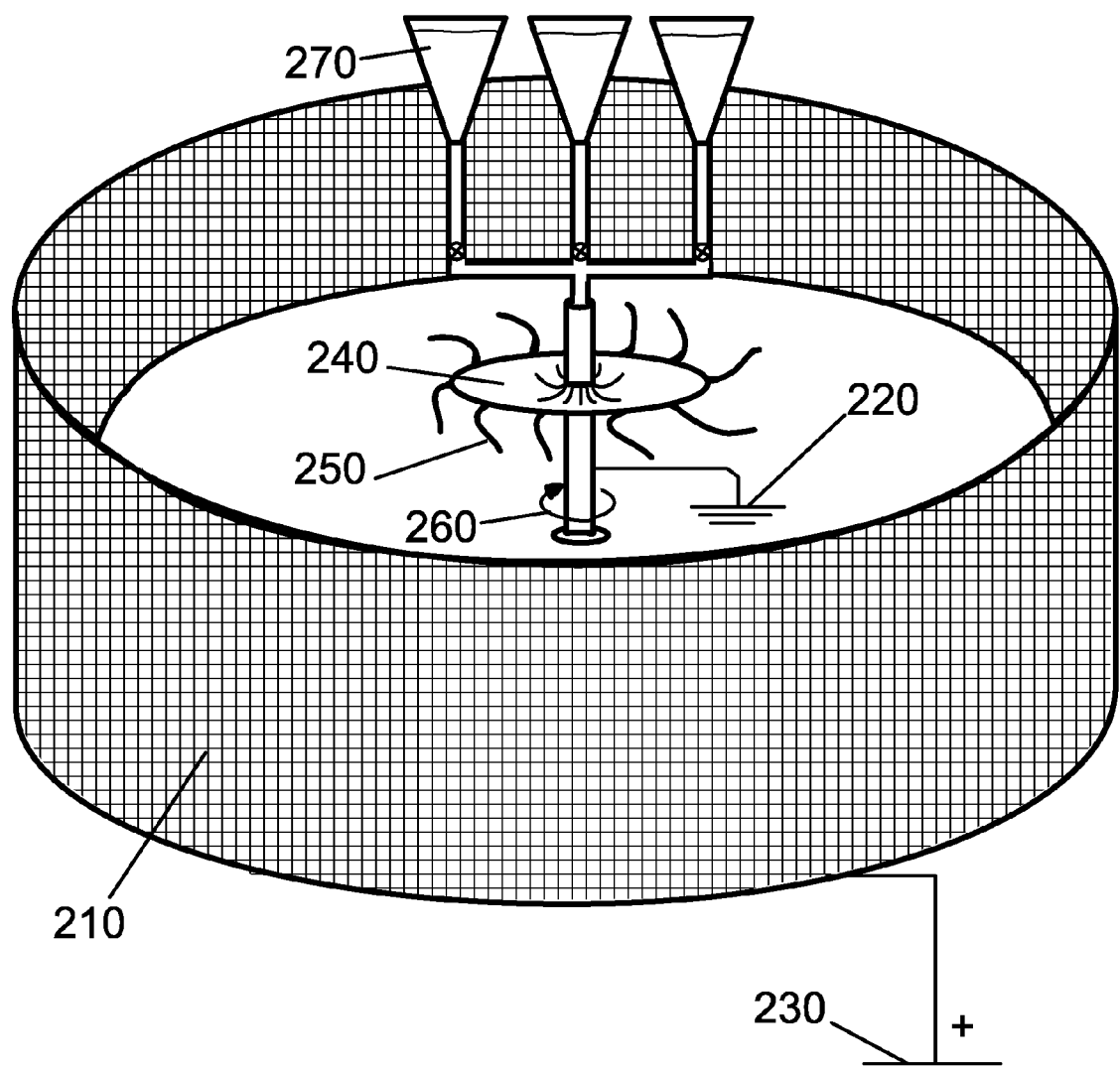
FIG. 2 illustrates the device used in the preferred embodiments of the invention.

FIG. 2 illustrates the apparatus used with the two preferred methods of the invention. The apparatus is essentially, a rotatable object (240), preferably having a disk shape as shown, at least one reservoir and tube assembly (270) to convey or introduce liquid at the center of the rotating disk on its surface, and a collector (210) or collection wall, typically a wire mesh surface surrounding the rotating disk to collect fibers created when liquid filaments (250) are spun off the edge of the disk. The rotating disk and the collection wall are at different electrical potentials, which aids in the formation and collection of the fibers. FIG. 2 shows the rotating disk at ground (220) and the collection wall having a positive electrical potential (230), but this may be reversed with the rotating disk at a positive electrical potential and the collection wall at ground.

The rotary object (240) encompassed in the invention may take any configuration that typically spins off liquid filaments that become fibers in transit to a collector. For example, the rotary object may utilize multiple disks stacked above one another to create a disk stack wherein each individual disk can spin off fibers. Further the rotating body may be of various shapes from a cup shape to an upside down bowl shape or any other shape that can spin off fibers. While there is no limit on rotating body diameter, for most preferred operations a disk is typically about 2 centimeters in diameter. Similarly, there is no limit on rotating body rotational speed and, for most preferred operations, a disk is rotating at a speed in the range of 300 to 100,000 revolutions per minute. Rotation (260) via its shaft, for example, may be achieved with pneumatic, electric or other forces.

While a single reservoir and tube assembly (270) might be used, FIG. 2 shows three reservoirs and tube assemblies connected in a flow delivery manifold to illustrate an embodiment with a plurality of reservoirs. In this case, holes around the circumference of a hollow rotational shaft introduce the liquid at the surface of the rotating object. Alternatively, tubes may extend down to close proximity of the surface. In either case, the flow delivery manifold simplifies the process of sequential coating of multiple fiber precursors and biological and abiological pro-coagulation factors. It enables manufacture of a customized formulation of a hemostatic bandage with one apparatus adding a sequence of coatings on the fibers by sequentially activating valves to halt the flow or deliver the materials from the separate reservoirs. For example, one reservoir and tube assembly may carry a solution of a biocompatible polymer, such as polylactic acid, the next one may carry a fibrinogen solution, and the third one may carry a thrombin solution.

The invention encompasses any configuration for the collector (210), even a less than optimal rectilinear wall that would not intercept all of the fibers or procoagulation species exiting the rotating body. The collector may be a moving circular belt, or a belt of other shapes that would permit continuous manufacture of bandages.

A typical satisfactory electrical potential difference between the rotating object and the collection wall is in a range of 3 to 60 kilovolts. The collector may be electrically positive and the rotating object a ground, or the collector may be at electrical ground and the rotating object electrically positive. The electrical potential difference maintained between the rotating object and the collector creates an electric charge on the matter conveyed from the rotating object to the collector, aids in formation of a liquid ligament and assists in conveying the fibers or coating material to the collector.

A magnetic field might also serve as an alternative to the electrical field in unique circumstances. For example, if a biocompatible procoagulant formulation has ferrofluidic properties, it could be accelerated toward the collector with a magnetic field instead of an electric field. However, this alternative is not preferred because magnetic forces are shorter range, and would thus require a large electromagnet to have the required influence on the fluid traveling from the disk to the collector.

Thus, in carrying out the methods of the invention, the operational parameters, such as disk rotational speeds, voltages and flow rates, can be adjusted from step to step to produce the desired results.

FIG. 1a illustrates the first preferred method that creates fibers having procoagulation species mixed within the fibers, which may then also be coated. FIG. 1b illustrates the second preferred method that creates fibers and coats them with procoagulation species.

FIG. 1a shows the steps in the first preferred embodiment of the invention in which a hemostatic dressing is made using a rotating object, typically a disk, to spin off fibers made from a liquid biocompatible fiber precursor introduced at the center of the rotating object. The fibers created by spin off from the disk are deposited on a collector positioned at a distance from the rotating object such that the fibers form a layer on the collector. Thus, four steps of this embodiment are: introducing a liquid biocompatible fiber precursor containing one or more active biological or abiological procoagulation species at the center of the rotating object such that the liquid can spin off the rotating object and form a first set of fibers (11a); depositing fibers from the first set of fibers onto a collector positioned at a distance from the rotating object such that a layer of fibers is created and wherein an electrical potential difference is maintained between the rotating object and the collector; (12a); introducing a liquid biocompatible fiber precursor containing one or more active biological or abiological procoagulation species different from those in step (a) at the center of the rotating object such that the liquid can spin off the rotating object and form a second set of fibers (13a); and, depositing fibers from the second set of fibers onto the collector (14a).

The first step (11a) of the first preferred embodiment is introducing a liquid biocompatible fiber precursor containing one or more active biological or abiological procoagulation species at the center of the rotating object such that the liquid can spin off the rotating object and form a first set of fibers. In this embodiment, the fiber precursor and the procoagulation species are mixed together so that when the fiber is produced, it contains one or more procoagulation species. The flow rate of liquid biocompatible fiber precursor is optimized usually as a function of the diameter of the rotating object, the distance to the collector and the evaporation rate of the solvent. A preferred flow rate of between 5 to 5,000 milliliters per hour is used for rotating objects having diameters in the range of 5 to 70 millimeters with a collector distance at about 30 centimeters. Solvents used in the invention to make the liquid biocompatible fiber precursor are chosen in part based on their ability to partially or totally evaporate during the time-of-flight of the charged matter traveling from the edge of the rotating disk to the collector, and the operator can optionally dry the fibrous mat deposited on the collector surface in several ways, such as vacuum or flowing air.

The second step (12a) of the first preferred embodiment is depositing fibers from the first set of fibers onto a collector positioned at a distance from the rotating object such that a layer of fibers is created and wherein an electrical potential difference is maintained between the rotating object and the collector. The collector is preferably a cylindrical wire mesh, but may be any surface capable of holding the fibers created by spin off from the rotating object. If wire mesh is used, the mesh size is preferably determined according to the desired texture of the fibrous mat. The distance of the collector from the rotating object is a function of the speed of rotation and the diameter of the rotating object. A distance in a range of about 5 to 100 centimeters for the edge-of-disk to collector is typically satisfactory. Optionally, the fibers deposited on the collector are actively dried.

The third step (13a) of the first preferred embodiment is introducing a liquid biocompatible fiber precursor containing one or more active biological or abiological procoagulation species different from those in step (a) at the center of the rotating object such that the liquid can spin off the rotating object and form a second set of fibers. The procoagulation species in this step are preferentially the ones that will react with those in the first step to form a clot when in the presence of blood. For example, if fibrinogen is used in the first step, then thrombin would be used in the third step.

The fourth step (14a) of the first preferred embodiment is depositing fibers from the second set of fibers onto the collector. The combined action of both the electric field created by the electrical potential difference and centrifugal forces created by rotation of the rotating body, spin off fibers from the rotating body toward the collector. The collector having been set at a distance to intersect the flight vector of the fibers catches the fibers and retains them as deposited on the collector. Optionally, the fibers deposited on the collector are dried before depositing fibers from the second set of fibers. Active drying may be accomplished by well known techniques, such as with flowing air or by drawing a vacuum.

Depositing fibers from the second set of fibers onto the collector may be performed such that the fibers from the second set of fibers are deposited over the fibers from the first set of fibers on the collector. This option might be elected when there is no chemical compatibility problem with doing so and to speed manufacturing of a dressing. Alternatively, the fibers may be deposited onto the collector at a location different from the fibers from the first set of fibers on the collector. This offers the opportunity to maintain chemical separation of the differently coated fibers until they are dry and to minimize the potential for chemical reaction between the two differing fibers. Also collection of the fibers from two sets at a different locations on the collector offers the opportunity to separately coat the fibers from the two sets with chemically incompatible procoagulation species and then combine the dry fibers from the first set of fibers with dry fibers from the second set of fibers.

FIG. 1b illustrates the steps in the second preferred method of the invention in which fibers are made from a liquid biocompatible fiber precursor by spinning off the rotating body. Then, the fibers are coated with procoagulation species. The steps of the second preferred method include: introducing a liquid biocompatible fiber precursor at the center of the rotating object such that the liquid can spin off the rotating object and form fibers (11b); depositing fibers so formed onto a collector positioned at a distance from the rotating object such that such that a layer of fibers is created and wherein an electrical potential difference is maintained between the rotating object and the collector (12b); and, coating the fibers with one or more procoagulation species (13b).

The first step (11b) of the second preferred embodiment is introducing a liquid biocompatible fiber precursor at the center of the rotating object such that the liquid can spin off the rotating object and form fibers. In this embodiment, the liquid biocompatible fiber precursor does not contain any procoagulation species. Optionally, the liquid biocompatible fiber precursor contains one or more active biological or abiological procoagulation species.

The second step (12b) of the second preferred embodiment is depositing fibers so formed onto a collector positioned at a distance from the rotating object such that such that a layer of fibers is created and wherein an electrical potential difference is maintained between the rotating object and the collector. This step is the same as in the first preferred embodiment as is explained above. Collection times and other operating variables are chosen so as to produce a desired average fiber diameter and fibrous mat thickness. Optionally, the fibers deposited on the collector are dried. Active drying may be accomplished by well known techniques, such as with flowing air or by drawing a vacuum.

The third step (13b) of the second preferred embodiment is coating the fibers with one or more procoagulation species. The coating step may be performed with any processes that actually coats the fibers, and preferably in submicron coatings, or molecular-scale coatings or dispersions. The preferred method of coating is introducing the procoagulation species at the center of the rotating object such that said liquid can spin off the rotating object and coat the fibers. This method is preferred because it uses the same apparatus to make the fibers and coat the fibers. Some proteins, e.g., factor XIIIa and fibrinogen, can be coated in the same step because of their chemical compatibility. Optionally, each coating may be dried before proceeding to another coating. The presence of solvents and/or moisture in the final ultrafine fiber based hemostatic bandage product is not necessarily something to be avoided. Rather, it is determined by the chemical compatibility and concentration of all active components in such liquid coating environments, and ease of manufacturing and packaging. For example, a hemostatic dressing based on biocompatible fibers and a soaking solution of fibrinogen, factor XIIIa, and possibly other biological and abiological blood coagulation species except for thrombin, may be suitable as a wet hemostatic patch.

Alternatively, the same apparatus can be used without rotation of the rotating body by simply adding dry particalized procoagulation species to the rotating body and allowing the electrical field to charge the particles and accelerate them from the disk to the fibers.

Alternatively, traditional nozzle electrospraying techniques may be employed using dry or wet procoagulant species. Electrospraying typically produces non-uniform and rough coatings on the fibers, but nevertheless produces a coating in the micron-range and can deposit submicron particles of procoagulant species onto the fibers. Dry electrostatic deposition of procoagulant powders is not preferred, unless they can be obtained as nanopowders.

Alternatively, a coating may be achieved by soaking the fibers in a solution containing the procoagulation species causing wet impregnation of the fibers followed by drying. One such method is disclosed in patent application PCT/IB2006/053526.

Alternatively, a coating may be achieved by introducing procoagulation species at the center of the rotating object while the rotating object is subjected to high frequency vibration. The high frequency vibration aids in formation of droplets and dispersal of the procoagulation species off the disk into a fine liquid spray.

Since dressings having fibrinogen and thrombin are highly desirable, an alternative preferred embodiment supplements the steps in the second preferred embodiment by including fibrinogen in the liquid biocompatible fiber precursor and then adding the steps of, (a) introducing, after coating the fibers with one or more procoagulation species, a liquid biocompatible fiber precursor that does not contain fibrinogen at the center of the rotating object such that the liquid biocompatible fiber precursor can spin off the rotating object and form a second set of fibers; (b) depositing fibers from the second set of fibers onto the collector; and, (c) introducing a thrombin solution at the center of the rotating object such that said solution can spin off the rotating object and coat the second set of fibers. The two sets of fibers on the collector may be deposited on top of each other or at separate locations on the collector. In either case, if these fibers are combined in a dressing, this combination or stacking of two layers of discrete fibers, one with fibrinogen within the fibers and a procoagulant species coating and the other one having a fiber not containing fibrinogen but having a thrombin coating.

These two distinct fiber sets may not be distinguishable to the naked eye and may comprise of two fibrous layers whose combined thickness is below one millimeter. Thus, while separation of the thrombin-containing and the fibrinogen-containing fibers avoids untimely thrombin-catalyzed formation of fibrin from fibrinogen in the event of moisture contamination during processing and packaging, each set of fibers is designed to be in very close proximity to the other, thereby permitting rapid mixing on total or partial redissolution of fibrinogen and thrombin on contact with blood from a wound.

EXAMPLE

Fibers produced by the second preferred embodiment are made from polylactic acid as the liquid biocompatible fiber precursor in solution with ethyl acetate as the solvent. In producing these fibers, positive electrical bias relative to ground electrical potential was applied to the cylindrical wire mesh collector enclosing the rotating disk, and the disk was placed at ground electrical potential, and at or near the center of the volume enclosed by the wire mesh collector. The liquid poured at the center of the disk was accelerated toward the edge of the disk by the combined action of both the electric field and centrifugal forces. Fibers such as those made from polylactic acid can be produced under the following conditions:

| | |
|---|---|
| Voltage | 20 kilovolts |
| Flow rate: | 200 milliliters per hour |
| Edge-of-disk to collector distance: | 30 centimeters |
| Disk diameter: | 2.0 centimeters |
| Rotational speed: | 36,000 revolutions per minute |
| Solution composition: | 100 grams of polylactic acid in one liter of ethyl acetate |
| Deposition time: | 30 minutes |
| Disk to liquid delivery outlet tube gap: | 1.5 millimeters |

In this example, a fibrinogen coating in the weight percent range of one to five percent on the polylactic acid fibers caused the surface of the fibers to have a rough texture. Fibrinogen concentration and all other processing variables are adjusted to produce the desired fibrinogen deposit morphology.

The fibrinogen solution can be atomized by the action of rotation, electric field and solvent evaporation into fibers, beaded fibers or particles that strike the pre-deposited polylactic acid fibers and coat them, or can be used to coat the fibers via the soaking methods disclosed in patent application PCT/IB2006/053526.

In testing, when the fibrinogen loaded fibers were contacted with an aqueous solution of thrombin, fibrin fibers were readily formed and entangled with the polylactic acid fibers. Entangling clearly shows the high surface area per unit weight of exposed active ingredients achieved in part through highly desirable scaffolding effects of the ultrafine fiber mats produced according to the invention. This micrograph shows that a single apparatus can be used to produce a fiber and coating whose structure is controlled at the micron and/or submicron level.

MODE FOR INVENTION

The following mode for the invention illustrates options and choices one might make in choosing chemically compatible solvents, procoagulants, and pre-deposited fibers. An ethanol solution of propyl gallate, the latter being a powerful platelet aggregator, may be used in a coating step to coat polylactic acid fibrous mats, but the processing conditions require that very little or no ethanol reach the fibrous mat to avoid undesirable polymer swelling effects leading to degradation of the mechanical quality of the finished hemostatic bandage product. The saturation concentration of propyl gallate in ethanol is approximately 50 grams per liter at room temperature. In the same manner, such ethanolic solutions of propyl gallate may be used in subsequent coating steps to apply a propyl gallate coating onto fibrinogen and/or thrombin loaded biopolymer fibers, but protein stability also requires that only propyl gallate and essentially no alcohol reach the fibers pre-coated with blood coagulation proteins. Use of different solvents and additives such as, but not limited to, glycerol and mannitol, which are known to compromise protein integrity less than ethanol, is within the scope of the invention. Alternatively, one may elect to dissolve the abiological procoagulation agent, such as propyl gallate, in water, and also in the presence of buffer salts that stabilize proteins and the procoagulation proteins, to coat the fibers with the abiological and biological procoagulation species in one step. Thus, two important factors to be considered in a decision on using one coating or two separate coatings, are chemical compatibility and the concentrations of the different active species for the hemostatic bandage that can be achieved in a single solution.

INDUSTRIAL APPLICABILITY

The invention has applicability to the medical treatment industries.

What is claimed is:

1. A method of making a hemostatic dressing using a rotating object comprising:

introducing a liquid biocompatible fiber precursor containing one or more active biological or abiological procoagulation species at the center of the rotating object such that the liquid can spin off the rotating object and form a first set of fibers;

depositing fibers from the first set of fibers onto a collector positioned at a distance from the rotating object such that a layer of fibers is created and wherein an electrical potential difference is maintained between the rotating object and the collector; and introducing a liquid biocompatible fiber precursor containing one or more active biological or abiological procoagulation species different from those in step at the center of the rotating object such that the liquid can spin off the rotating object and form a second set of fibers, such that the second set of fibers is deposited over the fibers from the first set of fibers on the collector.

2. The method of claim 1, further comprising the step of drying the fibers from the first set of fibers deposited on the collector before depositing fibers from the second set of fibers.

3. The method of claim 1, further comprising the step of coating the first set of fibers with one or more procoagulation species.

4. The method of claim 3, wherein the step of coating the first set of fibers with one or more procoagulation species is performed by a method selected from a group consisting of:

introducing said one or more procoagulation species at the center of the rotating object such that said liquid can spin off the rotating object and coat the first set of fibers;

spraying the first set of fibers using dry or wet electrospraying;

soaking the first set of fibers in a solution containing the said one or more procoagulation species causing wet impregnation of the first set of fibers; and introducing said one or more procoagulation species at the center of the rotating object while said rotating object is subjected to high frequency vibration.

5. The method of claim 3, wherein the liquid biocompatible fiber precursor is selected from a group consisting of polylactic acid, polylactic glycolic acid, chitosan, chitin, polycaprolactone, poly ethylene oxide, poly ethylene glycol, modified and unmodified polysaccharides, modified and unmodified synthetic polyaminoacids, proteins, poly beta-hydroxybutyric acid, poly beta-hydroxyvaleric acid, polydioxanone, polyphosphazene, poly ethylene terephthalate, poly tartronic acid, poly malic acid, random and block copolymers resulting from the polymers in the group and therapeutic agents that do not adversely affect the hemostatic function of the dressing and mixtures thereof.

6. The method of claim 3, wherein the liquid biocompatible fiber precursor contains one or more active biological or abiological procoagulation species.

7. The method of claim 3, wherein the liquid biocompatible fiber precursor contains fibrinogen and further comprising the steps of:

introducing, after coating the first set of fibers with one or more procoagulation species, a liquid biocompatible fiber precursor that does not contain fibrinogen at the center of the rotating object such that the liquid biocompatible fiber precursor can spin off the rotating object and form a second set of fibers;

depositing fibers from the second set of fibers onto the collector; and introducing a thrombin solution at the center of the rotating object such that said solution can spin off the rotating object and coat the fibers from second set of fibers on the collector.

8. The method of claim 3, wherein the rotating object is selected from a group consisting of a disk, a disk having an upward curve, a disk having a downward curve, and a plurality of disks spaced along a rotational axis of the rotating object.

9. The method of claim 3, further comprising the step of drying the first set of fibers deposited on the collector.

10. The method of claim 3, further comprising the step of drying the first set of fibers coated with said one or more liquid procoagulation species.

11. The method of claim 3, wherein the collector is made of wire mesh.

12. The method of claim 3, wherein the collector is in continuous motion.

13. The method of claim 3, wherein the liquid procoagulation species is a solution of one or more biological and abiological materials selected from a group consisting of fibrinogen, thrombin, prothrombin, prethrombin, von Willebrand factor, factor XIII, factor XIIIa, fibronectin, fibrin, aprotinin, antiplasmin, alpha-2 macro-globulin, plasminogen, alpha-1-antitrypsin, and plasmin activator inhibitors, calcium salts, propyl gallate and other gallic acid derivatives, epsilon aminocaproic acid, tranexamic acid, p-aminomethyl benzoic acid, and derivatives thereof.

14. A method of making a hemostatic dressing using a rotating object comprising:

introducing a liquid biocompatible fiber precursor containing one or more active biological or abiological procoagulation species at the center of the rotating object such that the liquid can spin off the rotating object and form a first set of fibers;

depositing fibers from the first set of fibers onto a collector positioned at a distance from the rotating object such that a layer of fibers is created and wherein an electrical potential difference is maintained between the rotating object and the collector;

introducing a liquid biocompatible fiber precursor containing one or more active biological or abiological procoagulation species different from those in step at the center of the rotating object such that the liquid can spin off the rotating object and form a second set of fibers, such that the second set of fibers is deposited onto the collector at a location different from the fibers from first set of fibers; and combining the fibers from the first set of fibers on the collector with the fibers from the second set of fibers on the collector.

* * * * *